United States Patent [19]

Coates

[11] Patent Number: 4,832,025

[45] Date of Patent: May 23, 1989

[54] THERMOPLASTIC SURGICAL SUTURE WITH A MELT FUSED LENGTH

[75] Inventor: Peter A. Coates, Sarisbury Green, England

[73] Assignee: American Cyanamid Company, Stamford, Conn.

[21] Appl. No.: 79,617

[22] Filed: Jul. 30, 1987

[51] Int. Cl.[4] ............................................. A61L 17/00
[52] U.S. Cl. ............................ 128/335.5; 128/334 R; 128/339; 623/13; 156/180; 156/181; 428/296; 57/243
[58] Field of Search ............... 128/334 R, 339, 335.5, 128/340; 623/1, 13; 156/180, 181; 428/296, 273, 274, 275; 57/243, 903

[56] References Cited

U.S. PATENT DOCUMENTS

| | | | |
|---|---|---|---|
| 3,317,924 | 5/1967 | Le Veen | 623/1 |
| 3,388,030 | 6/1968 | Estes et al. | 156/180 |
| 3,479,670 | 11/1969 | Medell | 128/334 R |
| 3,736,646 | 6/1973 | Schmitt et al. | 128/335.5 |
| 3,835,912 | 9/1974 | Kristensen et al. | 163/5 |
| 3,890,975 | 6/1975 | McGregor | 128/339 |
| 3,943,933 | 3/1976 | Gertzman | 128/335.5 |
| 3,980,177 | 9/1976 | McGregor | 206/63.3 |
| 3,981,307 | 9/1976 | Borysko | 128/339 |
| 4,510,934 | 4/1985 | Batra | 128/335.5 |
| 4,669,474 | 6/1987 | Barrows | 128/334 R |

FOREIGN PATENT DOCUMENTS 119287 9/1984 European Pat. Off. .

Primary Examiner—Richard J. Apley
Assistant Examiner—Paul Prebilic
Attorney, Agent, or Firm—Charles F. Costello, Jr.

[57] ABSTRACT

The invention is a multifilament thermoplastic surgical suture having a plurality of meltfused filaments where the filaments are only melt fused for a controlled length from at least one end of the suture. This melt fused end invention eliminates the end dipping operation for multifilament sutures. Preferably, the melt fused or bonded length of suture has at least eighty percent of the tensile strength of an unfused portion, as a substitute for the end-dipped suture.

13 Claims, 4 Drawing Sheets

THERMOPLASTIC SURGICAL SUTURE WITH A MELT FUSED LENGTH

BACKGROUND OF THE INVENTION

This invention relates to a multifilament thermoplastic surgical suture. Less than about fifty percent of the filaments are melt fused for a suitable controlled length. The controlled length is from at least one end of the suture. The melt fusion essentially seals and stiffens at least one end of the suture.

Most braided suture material, for needled and non-needled products, is skeined onto a frame, 'dipped' in a polymer resin solution, oven dried, cut off from the frame, and sorted for faulty lengths.

This operation is slow and messy, labor intensive and space consuming, and all that is achieved is the cutting of the sutures to length, the sealing of the ends to prevent fraying, and stiffening for greater ease of insertion into a needle. The average product spends 2 days of in-process time in the end dipping department.

This invention eliminates the end dipping operation for braided thermoplastic suture materials, and replaces it by an inline system in the next production operation (viz. needle attaching, or winding in the case of non-needle sutures) with a reduction of in-process time and floor space requirements.

For braided thermoplastic suture materials heat is used to achieve melt fusion of the outer filaments of the braid.

The braid is handled from the reel or spool as a controlled, continuous strand. Following melt fusion of the desired section of braid, it is cut to the required suture length and ready for additional processing.

The prevalent method for sealing (prevent brooming) and stiffening the cut ends of braided suture material involves use of the antiquated resin solution end-dipping system. FIG. 1 is a process flow chart describing this method. Examples of this process are given in U.S. Pat. Nos. 3,736,646 issued June 5, 1973; 3,890,975 issued June 24, 1975; and 3,980,177 issued Sept. 14, 1976. All of these patents are incorporated herein by reference.

The machine of this invention will fit onto an existing single operator, attach/wind workstation. The entire system control is automatic, including temperature control, knot detection and elimination, suture advancement to length, cutting etc. It has the following functions and features.

a. Sealing and stiffening of thermoplastic braided sutures by heat (melt-fusion) with a minimal degradation of tensile strength and a needle attachment strength equivalent to end-dipped sutures.

b. Measure to length by variable program, automatically controlled electric motor(s). A new innovation in length measurement is effected by driving the standard elastomer foam coated, figure eight winding rollers through discrete steps.

c. A totally new suture cutting concept has been developed, that of employing a razor blade slice/shear cutting across a hole in an anvil plate achieving a perfect end (i.e. retaining round cross section). The ends may be bias cut or straight cut, ready for insertion into a needle.

d. Automated knot detection and advance to the cutter, thereby saving an average of about one-half suture length per knot.

e. Automatically feed prepared strand to the operator or collect as a batch.

f. The new system is compact. The entire drive and cut unit can be held in the hand.

SUMMARY OF THE INVENTION

The invention is a multifilament thermoplastic surgical suture comprising less than about fifty percent of the filaments being melt fused for a suitable controlled length from at least one end of the suture. In one embodiment, less than about twenty-five percent of the filaments are fused. In a specific embodiment, less than about fifteen percent of the filaments are fused. In a more specific embodiment, about five to ten percent of the filaments are fused.

In another embodiment, the majority of the filaments being fused are on the surface of the suture. In yet another embodiment, the tensile strength of the controlled length is at least about eighty percent of the tensile strength of the remainder of the suture. Yet another embodiment is wherein the controlled length from an end of the suture is up to about one hundred millimeters. In a specific embodiment, the suture has a needle attached to at least a portion of the length. In a more specific embodiment, a needle is attached to both ends of the suture.

The invention is also a multifilament thermoplastic surgical suture comprising about five to ten percent of the filaments being melt fused for a length of less than about forty millimeters from at least one end of the suture. The tensile strength of the melt fused length is at least about eighty percent of the tensile strength of the remainder of the suture. In one embodiment the cut end surface proximal to the melt fused filaments is perpendicular to the axial centerline of the suture.

In another embodiment, the cut end surface proximal to the melt fused filaments is oblique to the axial centerline to the suture. In a specific embodiment, the end surface is about fifty to eighty degrees from said centerline. In a more specific embodiment, the surface is about sixty to seventy degrees from said centerline.

In yet another embodiment, the suture has a needle attached to at least a portion of the melt fused length. The needle can be a drilled end or flanged end needle.

In still another embodiment, the thermoplastic is selected from the group consisting of a polyester, a polyamide and a polyolefin. In one embodiment, the polyester is poly(glycolic acid). In a specific embodiment, the poly(glycolic acid) is a homopolymer. In another specific embodiment, the poly(glycolic acid) is a copolymer.

DESCRIPTION OF THE PREFERRED EMBODIMENT(S)

The overall system control as well as the individual process operations may be attained, in an automated fashion, by several means. In the preferred embodiment of this invention, the following are the means of choice:

1. The system is monitored and controlled by means of a microcomputer or a programmable logic controller (PLC).

2. Thermal 'sealing'/stiffening of thermoplastic braid suture mterials is performed by melt-fusion of the outer filaments using radiant/convective (i.e. non-contact) heater blocks. When closed, the blocks form a straight tunnel of circular cross-section to provide the braid with uniform thermal exposure,around its entire periphery. When the braid is advanced/indexed the blocks open in order to minimize the thermal exposure of the main suture body which is to be left untreated.

3. Braid advancement and suture length control is achieved by means of one or more pairs of apposed, elastomer-foam coated, friction rollers that are driven by a stepper motor. This provides accurate length control under moderate, controlled· tension, for a wide range of braid diameters, without abrasive damage.

4. Suture presence and knot detection is accomplished using adjustable intensity/sensitivity, through-beam optical sensor pairs.

5. Straight or bias cutting, without distortion of the braid cross-sectional shape is performed using an automatically actuated razor blade. It shear cuts across a hole in an anvil plate through which the braid protrudes.

Several of these means are described in greater detail below.

SUTURE THERMAL EXPOSURE

Figure 1:
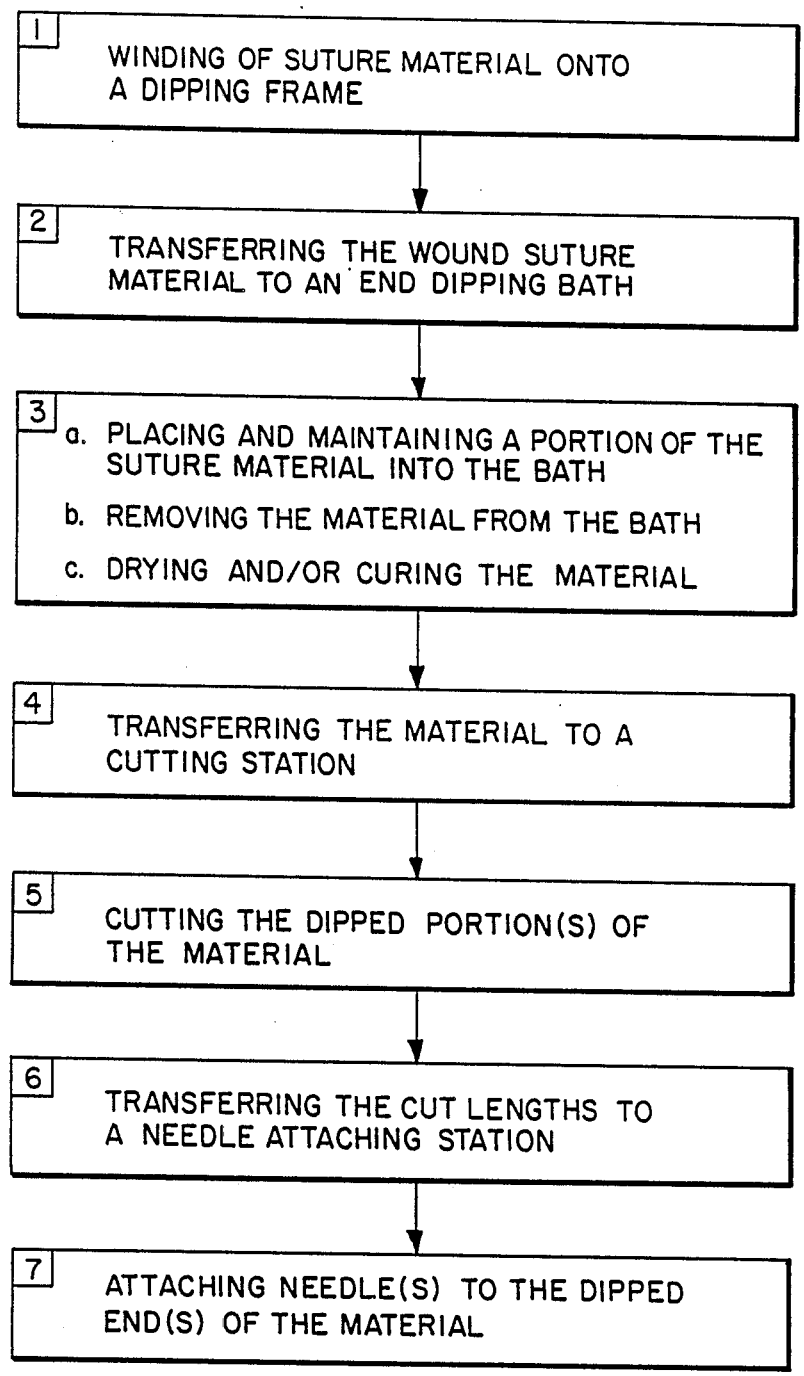
FIG. 1 is a block diagram showing the prior art steps for end dipping and needling a suture.
Figure 2:
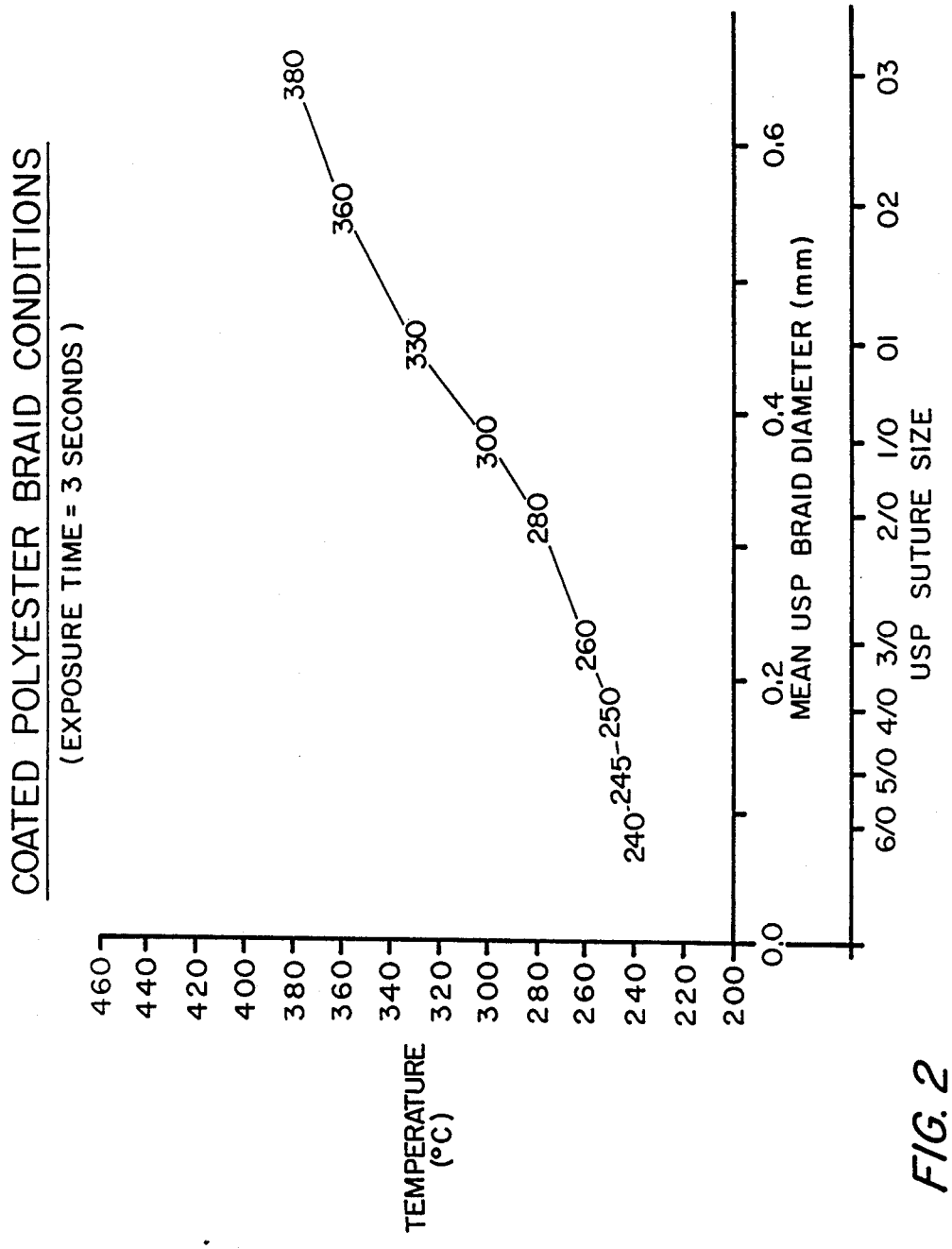
FIG. 2 is a graph showing the relationship between suture size and melt fusion temperature.

The appropriate treatment temperature and time for the braided suture in the heating tunnel varies according to the suture material and diameter. FIG. 2 shows the heating temperature versus optical braid diameter for a silicon coated polyester braided suture at an exposure time of three (3) seconds.

The exposure temperature and/or time must be increased with an increase in diameter of any given material. The required exposure temperature set point also varies directly with the heater tunnel diameter but is inversely related to the exposure time. Keeping all other parameters constant, there is a temperature range below which there is insufficient heat (radiation) in order to achieve any melting at all of the outer filaments, or above which there is almost total melt/fusion of the entire cross section of the suture material. For example, for a 4 mm diameter heating tunnel the temperature range would be about b 260° C. to 300° C. for such as a size 2/0 silicone coated polyester suture on a 3.0 second cycle.

MELT FUSION OF OUTER FILAMENTS

1. Initial Melting Action

The loose outer filaments that protrude from the basic outer diameter of the braid are initially melted back to the true outer diameter by the radiant heat. While this is not the same as the open flame singeing process commonly used for silk sutures, it does achieve the same result. The initial melting of loose filaments reduces or eliminates the resistance to an easy insertion into the needle's drilled hole.

2. Surface Filament Melt Fusion

After the initial melting of the protruding filaments, the material temperature rises enough to commence the melt fusion of the outer surface of the outer filaments. Note that only a small percentage (estimated to be 5–10%) of the outer filaments actually undergo surface melting and fuse with adjacent filaments at the respective contact points. FIG. 2 is a graph showing the relationship between USP (United States Pharmacopoeia Convention, Inc., MD U.S.A.) suture sizes and melt fusion temperatures.

Hence the suture stiffens on cooling but with only a comparatively small loss in strength. This melt fusion of the outer filaments has the effect of both:

a. Holding the filaments together when the stiffened section is cut, avoiding the brooming that would otherwise occur.

b. Stiffening the suture for ease of control and insertion into the drilled hole of a needle.

SUTURE END STIFFNESS

The stiffness of the heat treatable sutures can be increased by either:

a. increasing the temperature of the heating tunnel, or b. by reducing the diameter of the heating tunnel, or c. by increasing the dwell time in the tunnel. Table I shows the flexural stiffness measurements for USP size 3/0, silicone coated polyester braided sutures that have been heat stiffened at 260° C. (setpoint) for 3 seconds. The measurements were made using a Karl Frank Bending Stiffness Tester (Model No. 58963, Karl Frank GmbH, Weinheim-Birkenau, W. Germany). The higher measured stiffness of the heat stiffened sutures, as contrasted to the end-dipped ones, of Table 2, provides for ease of suture insertion into drilled end needles. This degree of stiffening is obtained with less than approximately 10% reduction in suture tensile strength. Higher or lower stiffness may, of course, be obtained as described above.

SUTURE DIAMETER REGULATION

In the current embodiment of this invention, the diameter of the stiffened suture section is regulated by controlling the braid tension during heating. Normally it is desired to maintain approximately the untreated suture diameter. While the stiffened end must be easily insertable into the standard drilled end needle, its diameter must not be reduced to the point of decreasing the needle attachment strength obtainable after swaging. The tension (during heat stiffening) required to achieve this varies with suture size, construction, material and previous thermal/drawing history. As indicated in Table 1, the appropriate heating tension for this particular example is approximately 40 to 80 g. Higher tensions during heating, generally cause a stretching of the braid with a concurrent reduction in diameter. Lower tensions, or free feed operation allows the braid to shrink axially and increase in diameter.

Table 2 shows the contrasting stiffness values for a prior art end-dipped suture.

TABLE 1

STIFFNESS
(Units = mN at 1 mm Suture Length)
Material = Silicone Coated Dacron Suture
Size = USP 3/0
PROCESS PARAMETERS:
TEMPERATURE SETPOINT = 260° C.
EXPOSURE TIME = 3 Sec.
BRAID TENSION = 40–80 g.
HEATER TUNNEL DIAMETER = 4 mm

| Sample No. | HEAT STIFFENED |
|---|---|
| 1 | 200 |
| 2 | 219 |
| 3 | 203 |
| 4 | 250 |
| 5 | 221 |

TABLE 1-continued

STIFFNESS
(Units = mN at 1 mm Suture Length)
Material = Silicone Coated Dacron Suture
Size = USP 3/0
PROCESS PARAMETERS:
TEMPERATURE SETPOINT = 260° C.
EXPOSURE TIME = 3 Sec.
BRAID TENSION = 40–80 g.
HEATER TUNNEL DIAMETER = 4 mm

| Sample No. | HEAT STIFFENED |
|---|---|
| 6 | 195 |
| 7 | 220 |
| 8 | 233 |
| 9 | 217 |
| 10 | 253 |
| 11 | 219 |
| 12 | 218 |
| 13 | 204 |
| 14 | 235 |
| 15 | 186 |
| | Avg. = 218 |
| | S.D. = 18 |

TABLE 2

STIFFNESS
(Units = mN at 1 mm Suture Length)
Material = Silicone Coated Dacron Suture
Size = USP 3/0

| Sample No. | END-DIPPED IN POLYMER RESIN SOLUTION* |
|---|---|
| 1 | 46 |
| 2 | 33 |
| 3 | 37 |
| 4 | 39 |
| 5 | 34 |
| 6 | 35 |
| 7 | 38 |
| 8 | 27 |
| 9 | 33 |
| 10 | 39 |
| 11 | 38 |
| 12 | 45 |
| 13 | 34 |
| 14 | 31 |
| 15 | 28 |
| | Avg. = 36 |
| | S.D. = 5 |

*TICRON ™ Suture (American Cyanamid Company, Wayne, NJ 07470 U.S.A.)

Figure 3:
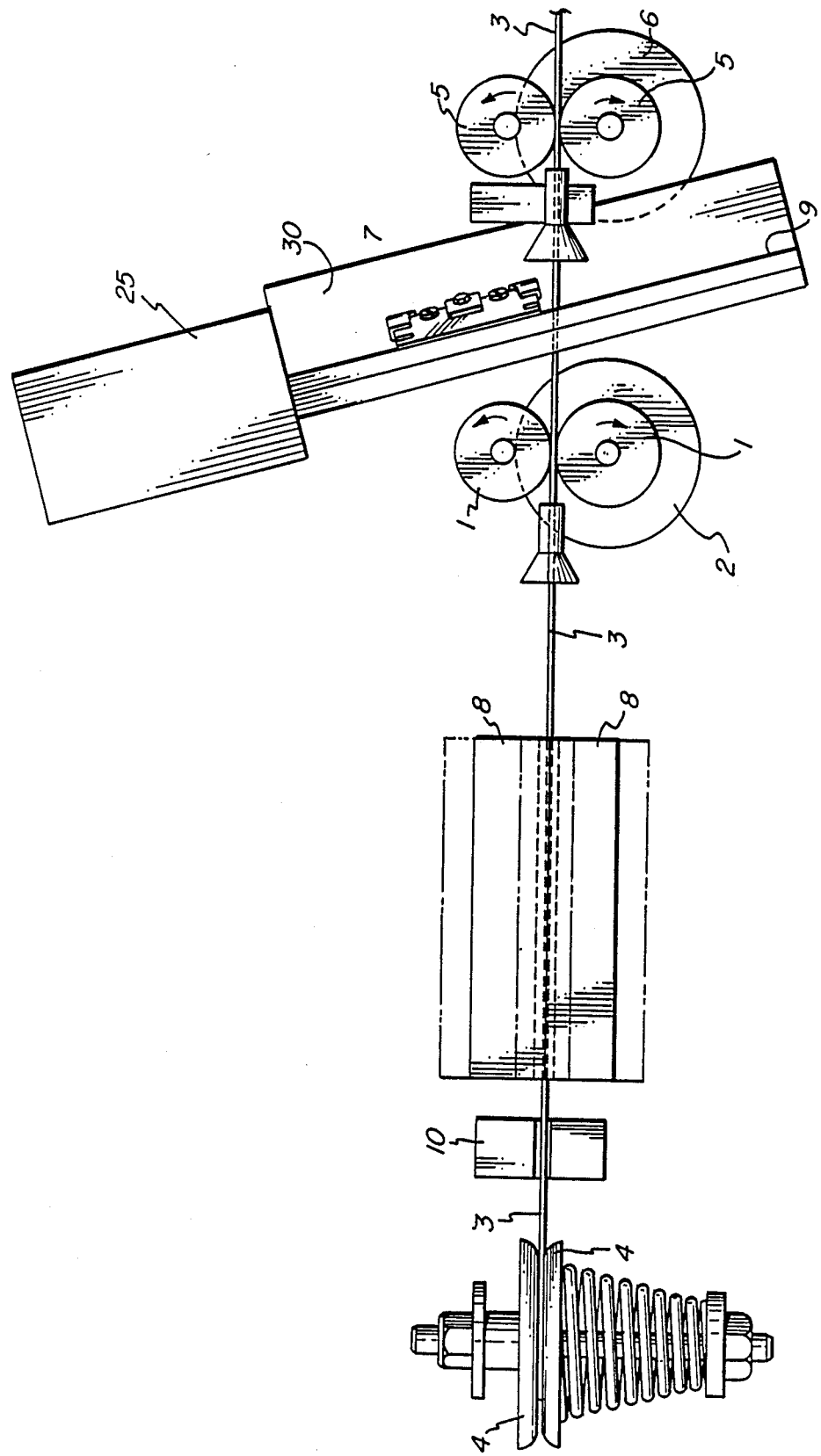
FIG. 3 is a schematic view showing the apparatus for melt fusing and cutting a suture end.

The means used for controlling the braid tension is illustrated schematically in FIG. 3. Upon entering the system a frictional 'drag' force is applied to the braid by a spring loaded pair of tension disks. Increasing the compression of the spring with the retainer nut, results in greater disk compression and a higher drag force on the braid. This may alternatively be achieved by any variable electromagnetic disks, mechanical or magnetic clutch or other tensioning device commonly used especially in the textile industry. Maintenance of the braid tension at the other end of the system (i.e. beyond the heater) is achieved by the pair of apposed, elastomer foamcoated friction rollers, one of which is driven by the stepper motor. These rollers are compressed against each other, by a spring or other means to exert a frictional 'drag' force on the suture which is advanced between them. This 'drag' force is at least equal to that of the tension disks, and usually greater, so that the suture advance may be controlled without slippage of the braid between the rollers.

As an alternative to the diameter regulation means described above in which braid tension is the controlled parameter, it is also possible to firmly clamp the braid at both ends of the heating tunnel and regulate the diameter by controlling the relative motion of the two clamps toward or away from each other. Although this clamp relative motion control is not yet quantified, the following principles are generally observed.

If the clamps are moved inwards, the portion of suture in the heating tunnell increases in diameter. If the clamps are held still when heating, the diameter reduces slightly. In order to maintain a constant diameter during heating, the clamps must move inwards a very small amount.

The amount of movement inwards and outwards in order to, for example, reduce the diameter by 10%, has not yet been established. This is currently being achieved by the controlled tension system described above.

None of the automated systems developed thus far contain a diameter measuring device. An optical sensor or other means may be incorporated in future machines with a feed back control loop.

Any of the diameter regulation means described here may be used in conjunction with the heat stiffening process to provide a number of suture product variants. One such product is a controlled release suture/needle combination as defined in The United States Pharmacopeia Twenty-first Rev. (hereafter abbreviated as USP), United States Pharmacopeial Convention, Inc., Rockville MD, U.S.A., 1984, Section 871. The lower needle holding strength may be obtained by a greater degree of thermal exposure (i.e. more suture strength degradation) or by reducing, the diameter of the stiffened section during heating by increasing the tension or by moving the clamps apart to stretch the braid.

Another product variant is a suture with a 1:1 needle-to-suture diameter ratio. The stiffened section of the braid is reduced in diameter during heating by using one of the techniques described above. Then, once cut, the reduced diameter end(s) may be inserted into a drilled end needle having essentially the same outside diameter as the main body of the suture. In surgery, the suture will then fill the hole left in the tissue by the needle.

SUTURE CUTTING

The primary objective in cutting the braid after heat stiffening is to obtain non-broomed ends that retain the approximately round cross-sectional shape of the braid. While this may be accomplished by various assemblies that differ in the design details, the concept embodied in this invention will be described here.

The location of the cutting assembly in this system is shown schematically in FIG. 3. One design that has been built and run successfully is shown in somewhat greater detail in FIG. 4.

The new suture cutting technique of this invention achieves the objective described above by means of the shearing action of a razor blade across an anvil plate. The suture is advanced through a tear-drop shaped hole in the anvil plate. The cutting edge of the razor blade is then driven (i.e. sheared) across the hole, in a straight or arcing motion, in such a manner that an acute angle (i.e. generally less than approx. 15°) exists between the edge and its direction of motion. As a result, the edge pushes the braid sideways into the end of the tear-drop shaped hole that has the smallest radius of curvature. With the contour of the braid supported by the hole in this way, further motion of the blade cuts the braid with minimal distortion of its shape. If the anvil plate, and therefore the blade's cutting plane, are perpendicular to the axial centerline of the braid a straight cut is obtained. Alternatively, a 'bias' cut may be obtained by inclining the anvil plate to the suture's axial centerline. It has been found empirically, that a bias cut made at an angle of about 60° to 70° to the suture's axial centerline, facilitates insertion into the needle without significant reducing the needle attachment strength. An angle significantly greater than about 70° does little to facilitate insertion into the needle drill hole. An angle significantly lower than about 60° would reduce the length of the suture end that is engaged by the swaged end of the needle, thereby lowering the needle attachment strength.

NEEDLE ATTACHMENT STRENGTH

The needle attachment strength data shown in Tables 3 and 4 indicate an essentially equivalent quality of attachment for the heat stiffened sutures in value for sutures heat stiffened by this invention and by means of end-dipping in a polymer resin solution. Both sets of results are well above the required average minimum of 0.68 kg (as per The United States Pharmacopeia Twenty-first Rev. (hereinafter abbreviated as USP), United States Pharmacopeial Convention, Inc., Rockville MO, U.S.A., 1984, Section 871) for this size (i.e. 3/0) suture. The sample Nos. in Tables 1 and 2 are identical. The sample Nos. in Tables 3 and 4 are identical. However, the sample Nos. 1 to 15 in Tables 1 and 2 are not necessarily identical to the sample Nos. 1 to 15 in Tables 3 and 4.

TABLE 3

NEEDLE ATTACHMENT STRENGTH
(Units = Kg.)
Material = Silicone Coated Dacron Suture
Size = USP 3/0
PROCESS PARAMETERS:
TEMPERATURE SETPOINT = 260° C.
EXPOSURE TIME = 3 Sec.
BRAID TENSION = 40-80 g.
HEATER TUNNEL DIAMETER = 4 mm

| Sample No. | HEAT STIFFENED |
|---|---|
| 1 | 1.603 |
| 2 | 1.581 |
| 3 | 1.337 |
| 4 | 1.619 |
| 5 | 1.728 |
| 6 | 1.559 |
| 7 | 1.624 |
| 8 | 1.635 |
| 9 | 1.722 |
| 10 | 1.660 |
| 11 | 1.607 |
| 12 | 1.529 |
| 13 | 1.414 |
| 14 | 1.478 |
| 15 | 1.474 |
| 16 | 1.504 |
| 17 | 1.716 |
| 18 | 1.553 |
| 19 | 1.707 |
| 20 | 1.501 |
| | Avg. = 1.578 |
| | S.D. = 0.106 |

TABLE 4

NEEDLE ATTACHMENT STRENGTH
(Units = Kg.)
Material = Silicone coated Dacron Suture
Size = USP 3/0

| Sample No. | END-DIPPED IN POLYMER RESIN SOLUTION* |
|---|---|
| 1 | 1.574 |
| 2 | 1.462 |
| 3 | 1.636 |
| 4 | 1.349 |
| 5 | 1.763 |
| 6 | 1.439 |
| 7 | 1.738 |
| 8 | 1.502 |
| 9 | 1.499 |
| 10 | 1.693 |
| 11 | 1.682 |
| 12 | 1.282 |
| 13 | 1.546 |
| 14 | 1.682 |
| 15 | 1.762 |
| 16 | 1.358 |
| 17 | 1.783 |
| 18 | 1.897 |
| 19 | 1.449 |
| 20 | 1.314 |
| | Avg. = 1.571 |
| | S.D. = 0.177 |

*TICRON ™ Suture (American Cyanamid Company, Wayne, NJ 07470 U.S.A.)

OVERALL SYSTEM OPERATION

Figure 4:
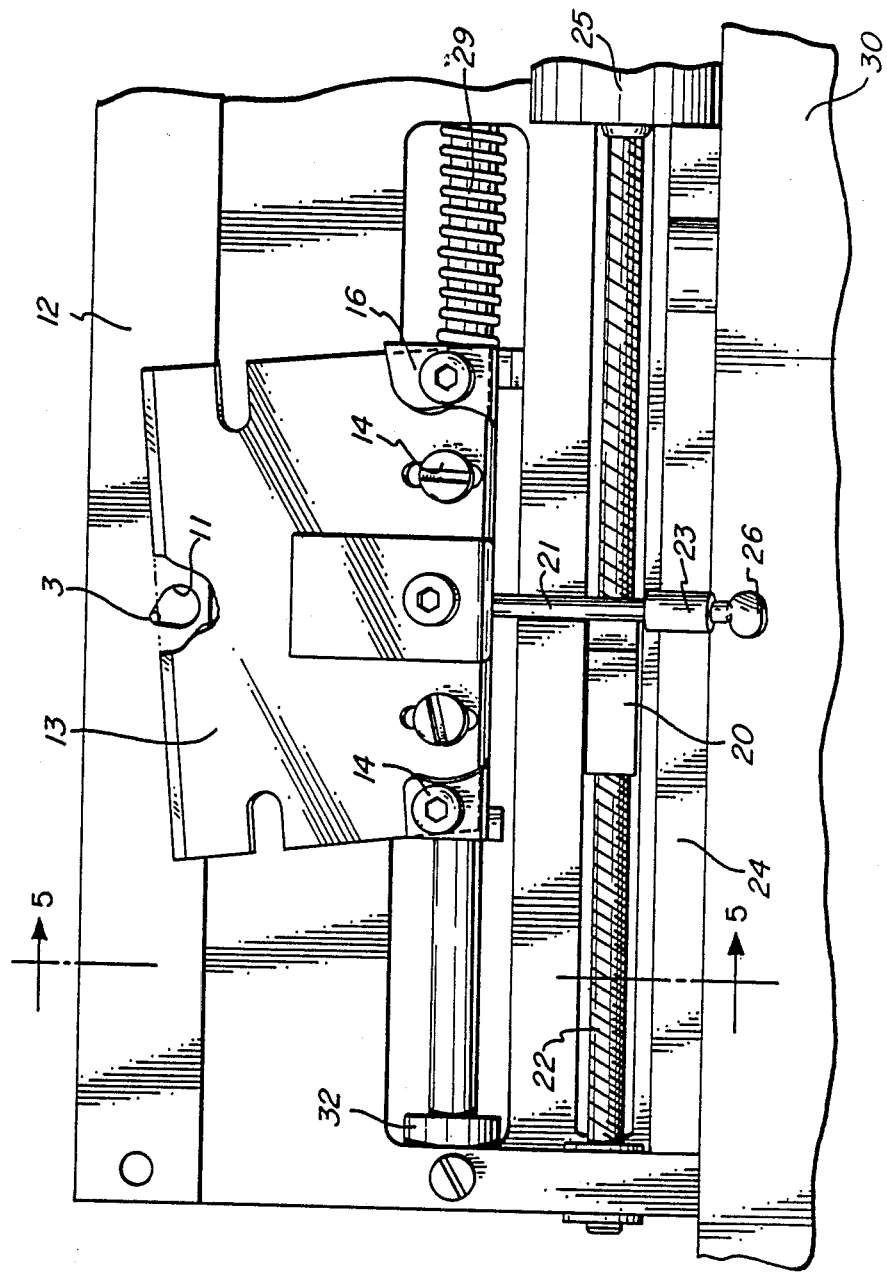
FIGS. 4 and 5 are broken front and cut away side views, respectively, of the cutting apparatus of FIG. 3.
Figure 5:
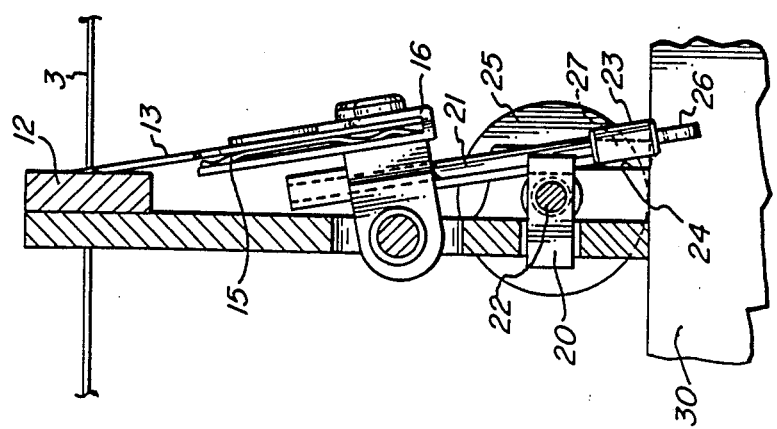

An apparatus of this invention is shown schematically in FIGS. 3 to 5. A pair of feed rollers 1, driven by a stepper motor 2, advance a suture braid 3 until a predetermined length is reached. Braid tension is maintained between these feed rollers 1 and the tension disk assembly 4 by the frictional drag force exerted on the braid at these two locations.

The second pair of friction (take-up) rollers 5 is driven by an electric DC motor or a stepper motor 6. These rollers take up the slack braid beyond the cutting assembly 7.

After the braid 3 is advanced to a predetermined suture length it is stopped. The heater blocks 8 close so that the section of braid to be heat-stiffened is enclosed, without physical contact, in the heater tunnel. Once the required exposure time is reached, the heater blocks 8 reopen and the feed rollers 1 advance the heat-stiffened section to the cutting assembly 7. Generally, the distance from the center of the heater blocks 8 to the cutting line 9 is adjusted to be equal to the desired suture length. This allows the next section of suture braid 3 to be heat-stiffened while the previous one is being cut. With the cut at the midpoint of each treated section of braid, a suture with both ends stiffened is manufactured, suitable for a double-armed product, i.e. having two needles.

Once the braid is cut, the take up rollers complete the advancement of the suture so that an operator may proceed with the next process step, such as needle attachment. Alternatively, the sutures may be collected as a batch for future additional processing.

FIGS. 4 and 5 specifically describe the cutting assembly 7. The cutting blade 13 can be adjusted by screws 14 to provide the desired shearing angle. Also, a spring clip 15 can optionally be placed in the cutting blade bracket 16 to assist in keeping the blade 13 against the anvil plate 12.

Referring further to FIGS. 4 and 5, a pusher 20 acts against a pin 21. The pusher 20 is moveably mounted on a threaded shaft 22, and is activated by an electric motor 25. A block 23 moves against a track 24, thus separating the pin 21 from the shaft 22. The point of contact between the block 23 and the track 24 can be adjusted by a set screw 26.

The pusher 20 acts against the pin 21 until the block 23 contacts the ramp 27. The block 23 then moves against the ramp 27 in approximately a diagonal motion (relative to the horizontal motion of the pusher 20) until the pin 21 clears the top of the pusher 20.

After the pin 21 clears the pusher 20, the blade 13 is forced across the opening 11 by the spring 29. The blade 13 is then arrested by a stationary block 30.

The pusher 20 is then moved down the threaded shaft 22 by the motor 25 and slides under the pin 21. The cycle can then be repeated for the next suture strand 3. As shown in FIG. 3, the cutting assembly 7 is oblique to the axial centerline of the suture braid 3. However, it is to be understood that the base 30 shown in FIGS. 3 to 5 is movable, and therefore the angular relationship of the cutting assembly 7 to the axial centerline of the suture braid can be varied. It is further to be understood that an actual showing of the various angular relationships is not necessary for an understanding of this invention.

Referring again to FIG. 3, if during braid advancement, a knot is detected by a through-beam optical sensor 10, the control system automatically causes the last "good" suture to be completed. It then advances the knot to a position just beyond the heater blocks 8. A new section is then heat-stiffened and the knot is subsequently advanced to just beyond the cut line 9. The take-up rollers 5 serve to aid in pulling the knot through the hole 11 (shown in FIG. 4) in the anvil plate 12 of the cutter assembly 7. The flawed section is then cut and the take up rollers 5 discharge it from the machine to be discarded. The normal process cycle is then repeated for the next "good" suture.

I claim:

1. A multfilament thermoplastic surgical suture having a plurality of meltfused filaments, the improvement comprising the filaments being meltfused for a length of less than about forty millimeters from at least one end of the suture, the tensile strength of the meltfused length being at least about eighty percent of the tensile strength of an infused portion of said suture.

2. The suture of claim 1 having a cut end surface at both ends of said suture, the suture further having an axial centerline, wherein the cut end surface proximal to the meltfused filaments is perpendicular to the axial centerline of said suture.

3. The suture of claim 1 having a cut end surface at both ends of said suture, the suture further having an axial centerline, wherein the cut end surface proximal to the meltfused filaments is olbique to the axial centerline of said suture.

4. The suture of claim 3 wherein said end surface is about fifty to eighty degrees from said centerline.

5. The suture of claim 4 wherein said end surface is about sixty to seventy degrees from said centerline.

6. The suture of claim 3 having a needle attached to at least a portion of said length.

7. The suture of claim 6 having a needle attached to both ends of said suture.

8. The suture of claim 6 having a drilled end needle.

9. The suture of claim 6 having a flanged end needle.

10. The suture of claim 1 or 6 wherein the thermoplastic is selected from the group consisting of a polyester, a polyamide, and a polyolefin.

11. The suture of claim 10 wherein the polyester is poly(glycolic acid).

12. The suture of claim 11 wherein the poly(glycolic acid) is a homopolymer.

13. The suture of claim 11 wherein the poly(glycolic acid) is a copolymer.

* * * * *